Feb. 4, 1975 R. YOSHIMURA Plant Pat. 3,680
AZALEA PLANT
Filed Aug. 2, 1973
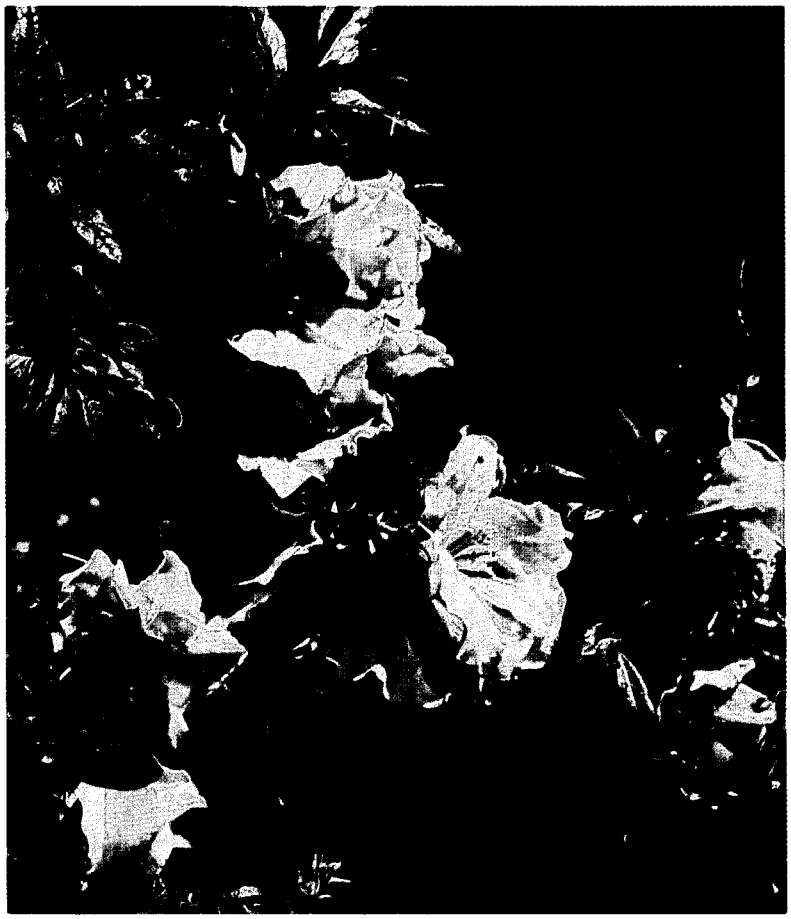

United States Patent Office

Plant Pat. 3,680
Patented Feb. 4, 1975

3,680
AZALEA PLANT

Raymond Yoshimura, 827 S. Gladys,
San Gabriel, Calif. 91772

Filed Aug. 2, 1973, Ser. No. 385,074
Int. Cl. A01h *5/00*
U.S. Cl. Plt.—56 1 Claim This invention relates to a new and distinct variety of azalea plant.

The plant resulted from cross breeding a variety of Belgian hybrid identified in the trade as Pink Pearl, a non-patented variety with a plant known as Alaska, also a non-patented variety. The original plant was produced by me in 1956, at San Gabriel, Calif., using Pink Pearl as the seed parent and Alaska as the pollen parent.

The flowers produced by the new variety are substantially campanulate in outline, are usually single with an occasional semi double bloom appearing. The general color of the blooms is a lavender rose. The principle blooming period for this new variety is usually in February and March in the costal regions of southern California. The plant has been observed to bloom sporadically throughout the year depending on the temperature and weather conditions. This plant is a vigorous predominantly upright variety.

Compared to its seed parent Pink Pearl, the flowers of the new variety are basically Persian Rose and have splotches of Magenta Rose as well as spots that are Chrysanthemum Crimson. The flowers are medium sized, campanulate and generally single. The flowers of the seed parent are predominantly pink, are larger and usually double.

Compared to its pollen parent Alaska, the above described flowers of the new variety clearly distinguish from those of the pollen parent. The flowers of the pollen parent are white, medium sized and are single.

The new variety can be grown either as an upright bush or it can be trained into a tree. This plant has been reproduced asexually by cuttings and graftings performed by me at San Gabriel, Calif. The resulting plants and their flowers have all exhibited the distinguishing characteristics of the new variety showing that the plants which resulted from these asexual reproductions have reproduced true. The new variety cannot be reproduced true from seed.

The accompanying drawings in full color show a typical specimen of the blooms and foliage. The colors are as true as it is possible to reproduce them by this type of color representation. A detailed description of the new variety of azalea plant follows and to facilitate identification of the important colors mentioned in the specification, the designation adopted by the British Horticultural Colour Charts has been followed.

THE FLOWER

Locality where grown and observed: San Gabriel, Calif.

Flowers borne: A number of flowers are borne on a stem.

Continuity: This variety will normally reach its peak blooming period in February and March in the coastal regions of southern California. The flowers will last on the plant from six to eight weeks. Blooms will appear sporadically throughout the year, depending on prevailing climatic conditions, however, the flowers produced at these times appear to have a much shorter life span than those that appear in February and March.

Bud:

*Before calyx breaks.*—Size: About three eighths of an inch in diameter and from one half to three quarters of an inch in length.

*As calyx breaks.*—Color: Predominantly green. Sepals: Shape: Substantially elliptic. Size: Vary from one half to three quaters of an inch in length.

*As first petal opens.*—Size: One and one half to one and three quarters inches in length with the width being slightly less. Color: The color is predominantly Persian Rose 628/3. Shape: The petals appear to be substantially round with the margin somewhat undulate. The petals are arranged compactly around the base and open considerably toward the tip.

Bloom:

*Size.*—The blooms are from two and one half to three inches at the widest part.

*Petalage.*—Petals vary from five to nine in number.

*Form.*—The bloom is campanulate becoming quite wide at the outer end.

*Petals.*—Shape: The petals are substantially orbicular at the outer end and become slightly pointed or more obtuse at the base. The margin is undulate. Color: The predominant color is Persian Rose 628/3, with splotches of Magenta Rose 027/1, and spots that are small and are colored Chrysanthemum Crimson 824/2.

*General color Effect.*—The general color effect is Persian Rose 628/3.

*Flower longevity.*—The flowers last up to eight weeks during the cooler months and seldom exceed three weeks duration during the warmer months.

REPRODUCTIVE ORGANS

Stamens: Stamens vary from eight to ten.

Filaments: Same number as stamens. Color: The filaments are slightly lighter than the flower.

Pollen:

*Quantity.*—Average quantity.

*Color.*—whitish.

Pistil: Each flower appears to have only one pistil (stigma, style, and ovary). Color: Stigma—Dark red; Style—Pink.

THE PLANT

Foliage:

*Leaves.*—Leaves are broadly elliptic with the tip apiculate and the base attenuate. The margin of the leaf is slightly ciliate. The surface of the leaves is slightly puberulent. Leaves are alternate.

*Petiole.*—Petiole is about five sixteenths inches long.

*Veins.*—Veins are pinnately arranged and are more prominent on the underside than on the upper surface. The back of the petioles and the back of the main veins are strigose.

*Size of leaves*—The leaves vary from seven eigths to one and seven sixteenths of an inch in width and from two and seven sixteenths to three and three eighths inches in length when fully matured.

*Color of leaves.*—Upper side of leaf: Parsley Green oo962. Underside of leaf: Spinach Green o960/3.

Growth habit: The plant is rated as a rapid grower and will develop up to twelve inches in one year during its early growth period. Plants have been known to reach a height of six feet. The variety can be grown either as an upright bush or as a tree.

Main stems: When trained as a bush, the main or principal stem can be up to one and one half inches in diameter. When trained as a tree the trunk will reach a diameter of one to one and one quarter inches.

Having described my invention, I claim:

1. The new and distinct variety of azalea plant substantially as herein shown and described, characterized particularly as to novelty by the single to semidouble, campanulate, medium sized blooms that are predominantly Persian Rose in color having splotches that are Magenta Rose and spots that are small and are colored Chrysanthemum Crimson borne in great profusion during the cooler months with many blooms on a stem, by the long life of the blooms particularly during the cooler months, and by its large leaves and vigorous growth habit.

No references cited.

ROBERT E. BAGWILL, Primary Examiner